US00RE42313E

(19) United States
(12) Reissued Patent
Erhan et al.

(10) Patent Number: US RE42,313 E
(45) Date of Reissued Patent: Apr. 26, 2011

(54) CHEMICALLY MODIFIED VEGETABLE OIL-BASED INDUSTRIAL FLUID

(75) Inventors: Sevim Z. Erhan, Peoria, IL (US); Atanu Adhvaryu, Peoria, IL (US); Zengshe Liu, Morton, IL (US)

(73) Assignees: The United States of America as repesented by the Secretary of Agriculture, Washington, DC (US); The Penn State Research Foundation, University Park, PA (US)

(21) Appl. No.: 11/147,470

(22) Filed: Jun. 7, 2005

Related U.S. Patent Documents

Reissue of:
(64) Patent No.: 6,583,302
Issued: Jun. 24, 2003
Appl. No.: 10/057,488
Filed: Jan. 25, 2002

(51) Int. Cl.
*C07C 59/00* (2006.01)

(52) U.S. Cl. ..... 554/213; 554/148; 554/149; 554/164; 554/227; 508/452

(58) Field of Classification Search ..... 508/452; 554/148, 149, 164, 213, 227
See application file for complete search history.

(56) References Cited

U.S. PATENT DOCUMENTS

| | | | |
|---|---|---|---|
| 3,035,069 | A | 5/1962 | Findley et al. |
| 5,164,124 | A | 11/1992 | Lange et al. |
| 6,121,398 | A | 9/2000 | Wool et al. |

OTHER PUBLICATIONS

Teeter, H.M., et al., "Synthetic Lubricants from Hydroxystearic Acids", *Industrial and Engineering Chemistry*, vol. 45, No. 8, pp. 1777–1779, Aug. 1953.

Gast, L. E., et al., "Synthetic Lubricants from Polyhydroxysteric Acids", *Industrial and Engineering Chemistry*, vol. 46, pp. 2205–2208, Oct. 1954.

*Primary Examiner*—Deborah D Carr
(74) *Attorney, Agent, or Firm*—Randall E. Deck; John Fado

(57) ABSTRACT

Triglyceride oils having unsaturated fatty acid substituents are modified to convert sites of unsaturation to C-2 to C-10 diesters. The resulting derivatives are characterized by thermal and oxidative stability, have low temperature performance properties and are environmentally-friendly. They have utility as hydraulic fluids, lubricants, metal working fluids and other industrial fluids. The triglyceride oils are most easily prepared via epoxidized vegetable oils which are converted to the diesters in either a one- or two-step reaction.

22 Claims, 1 Drawing Sheet

CHEMICALLY MODIFIED VEGETABLE OIL-BASED INDUSTRIAL FLUID

Matter enclosed in heavy brackets [ ] appears in the original patent but forms no part of this reissue specification; matter printed in italics indicates the additions made by reissue.

BACKGROUND OF THE INVENTION

1. Field of the Invention

This invention relates to a novel chemically modified vegetable oil-based industrial fluid having superior performance properties and to methods for its preparation.

2. Description of the Prior Art

Most of the lubricants currently in daily use originate from petroleum base stocks that are toxic to environment, making it increasingly difficult for safe and easy disposal. There has been a increasing demand for "green"lubricants [Rhee, I., NLGI Spokesman, 60(5):28 (1996)] in recent years due to concerns about loss of mineral oil-based lubricants to the environment and increasingly strict government regulations controlling their use. Losses from accidental spillage and non-recoverable usage can result in ground water contamination and pose a threat to animal and plant life.

Vegetable oils such as rapeseed oil and high oleic varieties of other oils are considered to be potential candidates to replace conventional mineral oil-based lubricating oils and synthetic esters [Randles, S. J. et al.; J. Syn. Lubr., 9:145 1992); Asadauskas, S. et al.; Lub. Eng., 52:877 (1996)]. Vegetable oils are non-toxic, renewable resources and lower cost alternatives to synthetic fluids. The primary industrial application of vegetable oil use has been in the area of biodegradable hydraulic fluids. They have very low volatility due to high molecular weight of triacylglycerol molecule and narrow range of viscosity change with temperature. The ester linkages deliver inherent lubricity and enable the oils to adhere to metal surfaces. Further, vegetable oils have higher solubilizing capacity for contaminants and additives than mineral base fluids.

The most serious disadvantage of vegetable oils is their poor oxidative stability [Becker, R. et al.; Lubr. Sci., 8:95 (1996); Gapinski, R. E. et al.; SAE Tech Pap. 941785, pages 1–9 (1994)], primarily due to the presence, of bis allylic protons. These protons arc highly susceptible to radical attack and subsequently undergo oxidative degradation to form polar oxy compounds. This oxy-polymerization process ultimately results in insoluble deposit formation, and an increase in oil acidity and viscosity. Vegetable oils also show poor corrosion protection [Ohkawa, S. A. et al.; SAE Tech paper 951038, pages 55–63 (1995)], and the presence of ester functionality render these oils susceptible to hydrolytic breakdown [Rodes, B. N., et al.; SAE Tech paper 952073, pages 1–4 (1995)]. Therefore contamination with water in the form of emulsion must be prevented at every stage. Low temperature studies have also shown that most vegetable oils undergo cloudiness, precipitation, poor flow and solidification at cold temperatures.

SUMMARY OF THE INVENTION

We have now discovered a novel class of chemically-modified vegetable oils and chemically-modified vegetable oil-based industrial fluids as well as methods for producing them from triglyceride oils having unsaturated fatty acid substituents. The resultant vegetable oil derivatives, having diester substitution at the sites of unsaturation, have utility in hydraulic fluids, lubricants, metal working fluids and the like.

In accordance with this discovery, it is an object of this invention to provide novel vegetable oil derivatives.

It is also an object of the invention to provide environmentally-friendly vegetable oil-based industrial fluids having acceptable low temperature performance properties.

It is a specific object of this invention to provide vegetable oil-based industrial fluids having acceptable thermal and oxidative stability and low temperature fluidity.

Another object of the invention is to introduce a new use for vegetable oils and to expand the market for an agricultural commodity.

A further object of the invention is produce industrial fluids that reduce the demand on petroleum resources and that are biodegradable.

It is also an object of the invention to provide both a single-step and a two-step synthetic route for converting sites of unsaturation in triglyceride fatty esters to diester functionality.

Other objects and advantages of this invention will become readily apparent from the ensuing description, dr

DETAILED DESCRIPTION

Figure 1:
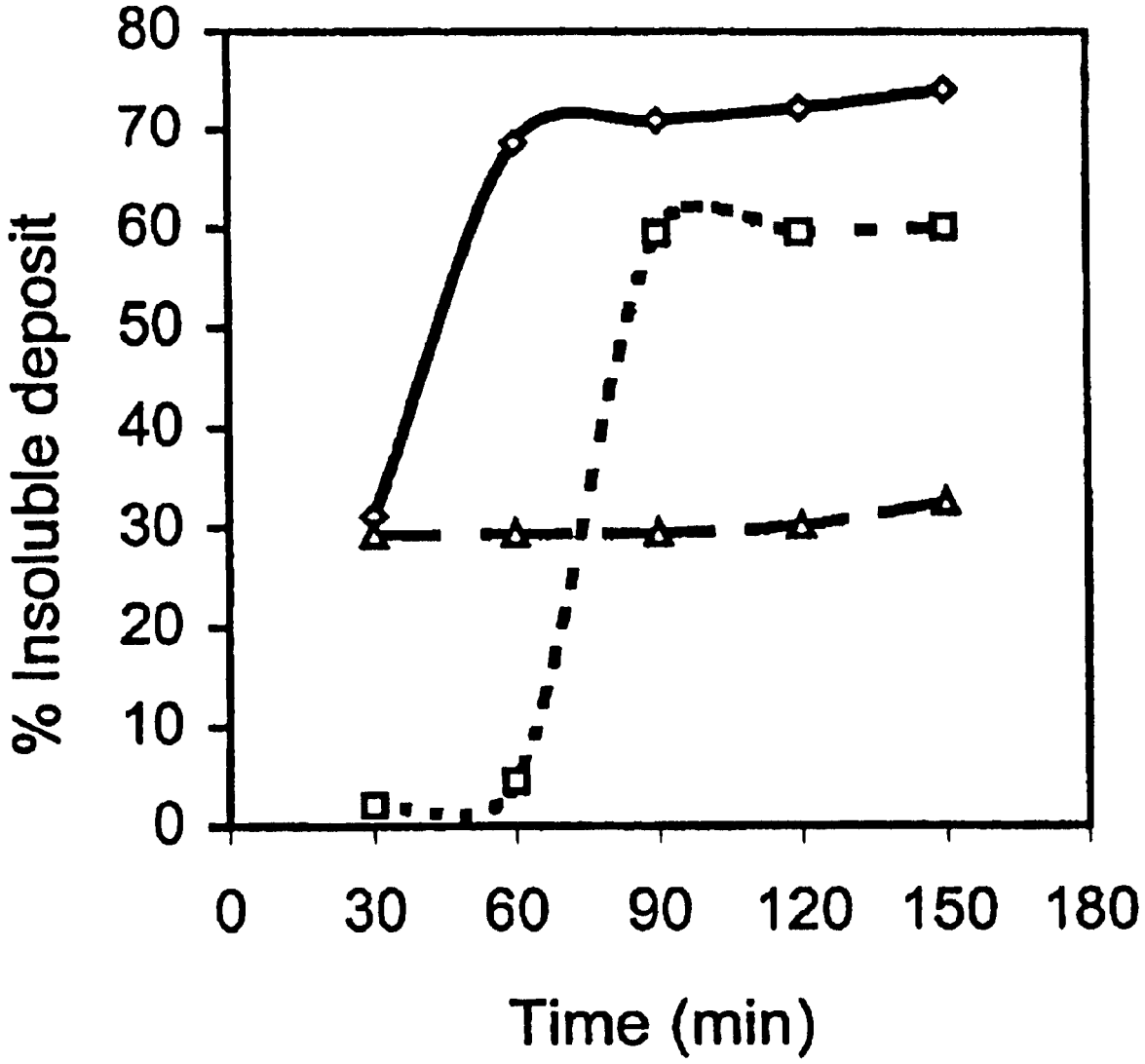
FIG. 1 is a graph comparing the percent of insoluble deposit of soybean oil (◇), epoxidized soybean oil (▭) and di-OHx-soybean oil (Δ) during thin film micro-oxidation (TFMO) at 175° C. under air flow (20 ml/minute).

The vegetable oil-based lubricants of the invention are prepared from triglycerides composed of fatty acid ester groups that collectively comprise at least one site of unsaturation. The oils principally contemplated herein include what are normally referred to as the triglyceride drying oils. The vegetable triglyceride drying oils include plant oils and plant source-like synthetic and semi-synthetic triglycerides that can be transformed into hard, resinous materials [see Encyclopedia of Polymer Science and Technology, H. F. Monk et al., eds., John Wiley & Sons, (1966), pages 216–234]. The expression "drying oils" is generic to both true drying oils, which dry (harden) at normal atmospheric conditions, and semidrying oils, which must be baked at elevated temperatures in order to harden. Unless otherwise indicated, "drying oil" will be used herein in its broadest sense to refer to both types of drying oil. The unsaturated fatty acids (linoleic or linolenic) of a drying or semidrying oil comprise double bonds that are readily available for entering into an oxidative reaction, or other reactions involved in the drying process. These oils may also include oleic fatty acids. Common sources of drying oils include cotton seed oil, castor oil, canola oil, linseed oil, oiticica oil, safflower oil, soybean oil, sunflower oil, corn oil, and tung oil. Of these oils, soybean oils is most readily available in both its unmodified and epoxidized state, and is therefore the most preferred. The properties of the subject industrial lubricants can be tailored by blending together different drying oils.

In order to render oxidative stability to the aforementioned triglyceride oils, it is essential that all, or substantially all (at least about 90%, and preferably at least about 95%), of the sites of unsaturation be modified by derivatization with a pair of short chain esters having a chain length in the range of C-2 to C-10, and preferably in the range of C-4 to C-8. The modified oil is characterized by the following formula:

Formula I

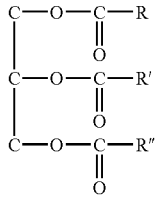

wherein R, R' and R" are independently selected from C-7 to C-21 aliphatic fatty acid residues, each including the structures:

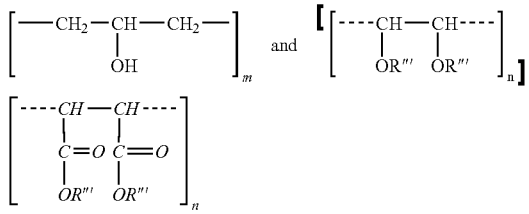

wherein R'" is H or C-2 to C-10 straight or branched hydrocarbon;

wherein the ratio of R'"=hydrocarbon:R'"=H in a given sample of modified triglyceride is at least 90:10;

wherein m=0–1;

wherein n=0–3; and wherein the average Σn for R, R' and R" in a given sample of modified triglyceride is at least 1.

In most of the common vegetable oils listed above, the triglyceride esters are composed of C-18 fatty acids, and accordingly R, R' and R" are C-17.

Vegetable oils have a tendency to form macro crystalline structures via a uniform stacking of the 'bent' triacylglycerol backbone at low temperature. Such macro crystals restrict easy flow of the system due to the loss of kinetic energy of individual molecules during self-stacking. The ester branching groups (R'") not only serve to eliminate the sites of unsaturation, but also impose spacing from other triglyceride molecules, thereby interfering with the formation of macro crystalline structures. The resultant modified triglycerides are characterized by enhanced fluidity, rendering them useful for the end-use applications envisioned herein. Triglycerides that are merely hydrogenated for the purpose of eliminating the sites of unsaturation will tend to harden at room temperature due to alignment and stacking of adjacent molecules. For this reason, it is important that there be at least one site of unsaturation available for derivatization that will yield two branching sites. The ester side chains that are most effective for imposing the desired molecular spacing and imparting the most desired pour point properties are those having a chain length of at least C6. However, the pour point and other functional properties of the derivatized oils are not significantly increased when the C-7 to C-10 branching chains are used.

The triglyceride oil is first either partially or completely epoxidized. The resultant oxirane rings are then available for cross-linking. Epoxidation may be carried out as described by Qureshi et al. [Polymer Science and Technology, Vol. 17, Plenum Press, page 250] or by any other method as known in the art. The degree of epoxidation should be such that there is at least 1, and preferably at least 2 oxirane rings per triglyceride molecule. Typically, the epoxidation is carried to completion. Epoxidized soybean oil, for example, would have 3–7 oxirane rings per molecule. Assuming complete conversion in the subsequent reaction(s), the value of n in Formula I, above, will coincide with the number of oxirane rings in the original epoxidized oil.

In what is described herein as the "one-step chemical modification" or "one step reaction scheme", the epoxidized oil is reacted in a single step reaction with an appropriate anhydride to yield the desired diester derivative. For the C-2 to C-10 diesters, the respective anhydrides would be acetic, propionic, butyric, valeric, hexanoic (caproic), heptanoic, octanoic (caprylic), nonanoic (pelargonic) and n-decanoic (capric). Boron [trifluride] *trifluoride* etherate or other suitable catalyst in an anhydrous solvent is used to simultaneously open the oxirane ring and activate the anhydride. At the completion of the reaction, the oxirane rings are quantitatively, or nearly quantitatively, converted to the diester derivative. This reaction is preferably conducted at elevated temperatures, usually exceeding about 40° C. With boron [trifluride] *trifluoride* etherate as the catalyst, the optimal conditions are 50° C. for about 3 hours.

In the two-step modification, the epoxidized oil is first refluxed in an aqueous solvent in the presence of a strong acid in order to hydrolyze the oxirane ring to a dihydroxy intermediate. The ring opening is predominantly the major reaction in this stage with minimal hydrolysis of the ester linkage. The retention of the triacylglycerol backbone is important for maintaining the biodegradability of the vegetable oil. A suitable acid for this purpose is perchloric. The triacylglycerol structure is largely preserved at temperatures less than 100° C. The dihydroxy compound exhibits a noticeable increase in viscosity over the epoxidized oil due to hydrogen bonding through the —OH pair.

In the second step, the dihydroxy derivative is reacted with the appropriate anhydride to yield the diester. The second step may take place at room temperature. For both steps, a combination of time and temperature is selected to insure that the reaction goes to completion, or nearly so (at least 90%). Both stages of the modification can be completed in 48 hours or less.

Whether the modified triglycerides of this invention are produced by the one-step or two-step modification, it is important that the ratio of diester derivative (where R'" is a C-2 to C-10 straight or branched hydrocarbon) to total number of unreacted, precursor functional groups (dienes, oxirane rings, and dihydroxy groups) is at least about 90:10.

As previously indicated and as demonstrated in the Examples, below, the modified triglycerides of this invention have superior properties which render them useful as hydraulic fluids. Other potential uses of these modified triglycerides are as biodegradable base stocks for lubricant applications, such as crankcase oils, drilling fluids, two-cycle engine oils, metal working fluids, wear resistant fluids, greases, and the like. Certain of these modified triglycerides meet or exceed many, if not all, specifications for some lubricant end-use applications without the inclusion of conventional additives. However, they may be formulated with other functional components, such as extreme-pressure additives, anti-wear additives, pour point depressants, other base stocks, diluents and the like. Determination of the requisite amount of additive for a particular application would be within the skill of a person in the art.

It is important for all of the end-use applications envisioned herein that the pour point of the subject modified triglycerides is below room temperature, and preferably below 0° C. As shown in the examples below, pour point temperatures as low as approximately −21° C. have been attained for certain derivatives. It is also important that the oxidative stability is reduced as compared to that of the unmodified oil. The thin film micro-oxidation method, described further below, provides one measure of oxidative stability. The percent of insoluble deposit indicates the amount of insoluble oxidizable material in a given oil. For example, the percent insoluble deposit for soybean oil is approximately 65%. It is desirable for the products of the invention to exhibit a percent insoluble deposit of less than 30%, and preferably less than 25%. Pressurized differential scanning calorimetry as described in further detail, below, is another method for measuring oxidative stability. The start ($T_S$) and onset ($T_0$) temperatures of oxidation obtained by this method are desirably higher than those for raw vegetable oil. $T_O$ is defined as the temperature when rapid increase in the rate of oxidation is observed in the system. The oxidation start temperature ($T_S$) is the temperature during which primary oxidation products begin to form in the vegetable oil matrix. $T_S$ is also an indication of loss of small molecular fragments due to evaporation.

The following examples are intended to further illustrate the invention, without any intent for the invention to be limited to the specific embodiments described therein.

EXAMPLE 1

Two-step Triglyceride Modification Synthesis of di-hydroxylated soybean oil (di-OH-SBO) from epoxidized soybean oil (ESBO).

Epoxidized soybean oil (ESBO) was obtained from commercial sources (purity level of 98%) and was used without any further purification. Perchloric acid ($HClO_4$, 70%, ACS reagent) was used as a ring opening catalyst.

The reaction was carried out by refluxing a 2450 ml aqueous solution of 127.4 gm epoxidized soybean oil at 100° C. for 48 hours, in a three-neck 5000 ml round bottom flask. Perchloric acid (26.05 gm) was added drop-wise to the reaction mixture that was constantly agitated by a mechanical stirrer. After the reaction was complete, the mixture was cooled to room temperature and the organic phase was extracted with chloroform ($CHCl_3$) and washed three times with water to remove any traces of acid remaining in the reaction mixture. The solvent was removed under reduced pressure at 80° C. and the product was stored under dry vacuum overnight.

Synthesis of di-OHexanoyl-soybean oil (di-OHx-SBO) from di-hydroxylated soybean oil (di-OH-SBO).

Forty gm of di-OH-SBO was added to 40 gm of hexanoic anhydride in 1:1 ratio, and 19.97 gm of pyridine in equimolar ratio was further added to the reaction mixture. The mixture was stirred with a mechanical stirrer in a 500 ml glass round bottom flask for 48 hours at room temperature. Then the reaction solution was poured into ice water and again stirred for 12 hours. The reaction mixture was extracted several times with solvent diethyl ether. Then the organic phase was washed with 100 ml 3% HCl and 5% $NaHCO_3$ (each 3 times) and finally dried over anhydrous $MgSO_4$ for 24 hours. The solvent was removed under reduced pressure at 80° C. and the product stored under vacuum.

Synthesis of di-OAcetoxy-soybean oil (di-OAc-SBO) from di-hydroxylated soybean oil (di-OH-SBO).

The procedure used for the production of di-OHx-SBO was repeated, except that acetic anhydride was substituted for the hexanoic anhydride.

Synthesis of di-OButoxy-soybean oil (di-OBu-SBO) from di-hydroxylated soybean oil (di-OH-SBO).

The procedure used for the production of di-OHx-SBO was repeated, except that butyric anhydride was substituted for the hexanoic anhydride.

EXAMPLE 2

One-step Triglyceride Modification Synthesis of di-OHexanoyl-soybean oil (di-OHx-SBO) from epoxidized soybean oil (ESBO).

In a dry three-neck 500 ml round bottom flask fitted with a condenser were placed 50 gm of ESBO, 46.88 gm of hexanoic anhydride (1:1 equivalent ratio) and 400 ml of methylene chloride ($CH_2Cl_2$). The mixture was stirred and the temperature maintained at 50° C. under dry $N_2$ atmosphere. Boron [trifluride] *trifluoride* etherate ($BF_3$ ether)(8–10 drops) were added and the mixture was stirred and refluxed for 3 hours. After the reaction mixture cooled to the room temperature, it was washed 3 times each with 5% $NaHCO_3$ solution followed by brine solution. Later, the mixture was dried over anhydrous magnesium sulfate (overnight). It was then filtered and evaporated under reduced pressure to recover the di-OHx-SBO.

Molecular Analysis.

Products were subjected to NMR analysis to identify and compute the relative distribution of —$CH_n$— (n=0"3) carbons in the various reaction products. NMR spectra (not shown) indicate that absorbance due to epoxy group is absent in di-OH-SBO and di-OHx-SBO. The relative intensity of terminal methyl group (δ 0.8–1.0 ppm) is significantly higher in di-OHx-SBO as compared to ESBO. The absence of the peak at δ 1.4–1.55 ppm in di-OHx-SBO suggest that epoxy carbons of ESBO are now the branching sites for side chains in di-OHx-SBO.

The presence of functional groups were monitored using FTIR analysis. Absence of absorption at 822 $cm^{-1}$ due to the epoxy group indicates that the starting material undergoes complete ring opening with the consequent generation of free —OH group resulting in dimeric (3550–3400 $cm^{-1}$) and smaller amount of polymeric (3400–3200 $cm^{-1}$) association through H-bonding.

Thin Film Micro-oxidation (TFMO) Method.

A small amount of oil (25pL) was oxidized under thin film conditions on an activated high carbon steel catalyst surface with a steady flow (20 $cm^3$/minute) of dry air passing over the heated sample. The oxidation was carried out at constant temperature (175±1° C.) inside a bottomless glass reactor. After a specified time length, the catalyst with the oxidized oil sample was removed from the oxidation chamber and cooled rapidly under a steady flow of dry $N_2$ and immediately transferred to a desiccator bottle. Later (approximately 2 hours), the catalyst was weighed for sample loss due to evaporation (or gain due to oxidation) and then soaked (30 minutes) with tetrahydrofuran solvent to dissolve the soluble portion of oxidized oil. The catalyst containing the insoluble deposit was placed in a desiccator for complete removal of trace solvent. After 2 hours, the catalyst samples were weighed to determine the amount of insoluble deposit.

As shown in FIG. 1 the TFMO data reveals that epoxidation of, —C═C— bonds in SBO resulted in a product (ESBO) characterized by a low insoluble deposit until 1 hour into the oxidation process. Thereafter, a sharp increase in the deposit formation suggests a catastrophic breakdown of the epoxy group leading to oxidative polymerization reaction through the reactive oxygen radical thus generated. The presence of branching in di-OHx-SBO lowers the initial thermal and oxidative stability of the oil as compared to ESBO (Table 1), however the deposit-forming tendency remained fairly low and constant throughout the test.

Pressurized Differential Scanning Calorimetry (PDSC) method.

As a measure of oxidative stability, samples were subjected to PDSC using a DSC 2910 thermal analyzer (Table 2, top). Nominally 1.5 mg of sample was placed in a hermetically sealed type aluminum pan with a pinhole lid for interaction of the sample with the reactant gas (dry air). A film thickness of less than 1 mm was required to ensure proper oil-air interaction and eliminate any discrepancy in the result due to gas diffusion limitations. Dry air (obtained commercially) was pressurized in the module at a constant pressure of 3450 KPa and the scanning rate was a constant 10° C./minute. The start ($T_S$) and onset ($T_0$) temperatures of oxidation were obtained from the reaction exotherm in each case. $T_0$ is obtained from extrapolating the tangent drawn on the steepest slope of reaction exotherm. High $T_0$ and $T_S$ would suggest a high oxidative stability of the vegetable oil matrix.

Pour Point Method.

Pour points were determined by following the ASTM D 97 (1997) method using 50 ml samples. Temperatures were measured in 3° C. increments at the top of the sample until it stopped pouring. Pour point values for SBO, ESBO, and each of the modified triglycerides are given in Table 3. The SBO has a pour point of −6° C., while ESBO freezes at 0° C. The thermal and oxidative stabilities of ESBO due to the removal of —C═C— unsaturation, however, are at the expense of desirable fluidity properties at cold temperatures. Attachment of at least a C-5 side chain at epoxy carbon sites improves the pour point significantly, as demonstrated by the superior pour point for di-OHx-SBO (−18° C. to −21° C.).

EXAMPLE 3

Pour Point of di-OHx-SBO Formulations

Further improvement in the low temperature fluidity of di-OHx-SBO as prepared in Examples 1 and 2 was tested in a formulation comprising pour point depressant (PPD) additives, including sunflower oil, mineral oil and proprietary compounds (Table 4). Blending was carried out by stirring chemically modified oil with an optimized additive dose at room temperature for 2 hours. The purpose of the PPD additives was to sterically hinder crystallization of triacylglycerol molecules at low temperature bydisrupting the stacking mechanism. An optimum PPD additive concentration of 1% in the final blend enabled a pour point of −30° C. for di-OHx-SBO. Further addition of PPD additives made no significant improvement in the pour point. Similarly, an optimized concentration of 1% antioxidant (AO) additive (mixture of an alkylated phenol and proprietary compounds) was added to the final blend.

Oxidative stabilities of formulations containing diluent and diluent with AO were determined by the PDSC method described in Example 1. The results are reported in Table 2 (bottom).

EXAMPLE 4

Low Temperature Storage Stability of di-OHx-SBO Formulations

The same experimental setup (ASTM D 97) as used for pour point determination in Example 1 was adopted for low temperature stability measurements. The samples were kept at −25° C. and visually inspected every 24 hours for 7 days for fluidity (similar to pour point determination). Failing criteria consisted of crystallization, solidification and formation of solid particles but did not include haziness and loss of transparency.

The (di-OHx-SBO) formulated with PPD was susceptible to freezing when held for 3 days at −25° C. In order to improve the cold storage stability of the formulation over an extended time period, a biodegradable synthetic ester, dibutyl adipate (96% purity) was uniformly blended into the formulation as a diluent at several concentrations. The final optimized formulation di-OHx-SBO+1% PPD+1% AO+diluent (70:30 oil:diluent ratio) that had a pour point of −42° C. passed the 7 days storage stability test at −25° C.

TABLE 1

Thin Film Micro Oxidation of Soybean Oil Modifications[a]

| Test oils[b] | % Volatile loss | % Insoluble deposit |
|---|---|---|
| SBO | 12.17 | 65.85 |
| ESBO | 7.02 | 9.53 |
| OAc-SBO | 12.09 | 9.14 |
| OBu-SBO | 28.02 | 15.07 |
| di-OHx-SBO (2-step) | 57.83 | 28.33 |
| di-OHx-SBO (1-step) | 52.47 | 22.12 |

[a]Conducted at 175° C., 25 μL, 1 h;

[b]SBO = Soybean oil; ESBO = Epoxidized soybean oil; OAc-SBO = Acetoxy-SBO; OBu-SBO = Butoxy-SBO; di-OHx-SBO = Hexanoyl-SBO

TABLE 2

Pressurized Differential Scanning Calorimetry at 10° C./min

| Test oils[a] | Start temperature ($T_s$) ° C. | Onset temperature ($T_o$) ° C. |
|---|---|---|
| SBO | 161.3 | 178.2 |
| ESBO | 177.4 | 203.9 |
| OAc-SBO | 135.7 | 165.1 |
| OBu-SBO | 140.1 | 170.2 |
| di-OHx-SBO (2-step) | 171.9 | 196.6 |
| di-OHx-SBO (1-step) | 173.7 | 196.3 |
| Formulations: | | |
| di-OHx-SBO (2-step):diluent (70:30) | 172.9 | 194.5 |
| di-OHx-SBO (2-step):diluent (70:30) + additive (1% AO) | 201.1 | 215.2 |

[a]SBO = Soybean oil; ESBO = Epoxidized soybean oil; OAc-SBO = Acetoxy-SBO; OBu-SBO = Butoxy-SBO; di-OHx-SBO = Hexanoyl-SBO; AO = Antioxidant

TABLE 3

Pour Points[a] of Soybean Oil Modifications

| Test oils[b] | Pour point (° C.) |
|---|---|
| SBO | −6 |
| ESBO | 0 |
| OAc-SBO | −3 |
| OBu-SBO | −3 |
| di-OHx-SBO (2-step) | −18 |
| di-OHx-SBO (1-step) | −21 |

[a]ASTM D 97;

[b]SBO = Soybean oil; ESBO = Epoxidized soybean oil; OAc-SBO = Acetoxy-SBO; OBu-SBO = Butoxy-SBO; di-OHx-SBO = Hexanoyl-SBO

TABLE 4

Pour Points[a] of di-OHx-SBO Formulations

| Test oil[b] | PPD[c] (%) | Diluent:oil (ratio) | Pour point (° C.) |
|---|---|---|---|
| di-OHx-SBO (2-step) | 0 | 0:100 | −18 |
| di-OHx-SBO (2-step) | 1 | 0:100 | −30 |
| di-OHx-SBO (2-step) | 1 | 30:70 | −42 |
| di-OHx-SBO (1-step) | 2 | 40:60 | −45 |

[a]ASTM D 97;
[b]di-OHx-SBO = Hexanoyl-SBO;
[c]PPD = Pour point depressant

We claim:

1. A modified vegetable triglyceride characterized by the following formula:

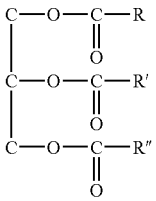

wherein R, R' and R" are independently selected from C-7 to C-21 aliphatic fatty acid residues, each including the structures:

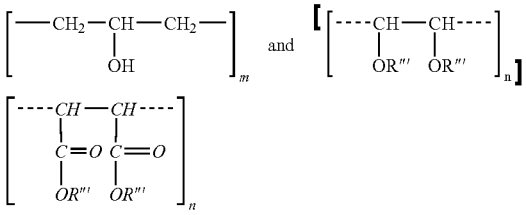

wherein R'" is H or C-2 to C-10 straight chain or branched hydrocarbon;

wherein the ratio of R'"=hydrocarbon:R'"=H in said modified triglyceride is at least 90:10;

wherein m=0–1;

wherein n=0–3; and wherein the average Σn for R, R' and R" in said modified triglyceride is at least 1.

2. The modified vegetable triglyceride of claim 1, wherein R, R' and R" are C-17 aliphatic fatty acid residues.

3. The modified vegetable triglyceride of claim 1, wherein the average Σn for R, R' and R" in said modified triglyceride is at least 3.

4. The modified vegetable triglyceride of claim 1, wherein the average Σn for R, R' and R" in said modified triglyceride is in the range of 3–7.

5. The modified vegetable triglyceride of claim 1, wherein R'" is a C-4 to C-8 straight chain hydrocarbon.

6. The modified vegetable triglyceride of claim 1, wherein R'" is a C-6 straight chain hydrocarbon.

7. The modified vegetable triglyceride of claim 1, wherein m=1.

8. A modified vegetable triglyceride of claim 1, wherein said vegetable triglyceride is selected from the group consisting of cotton seed oil, castor oil, canola oil, linseed oil, oiticica oil, safflower oil, soybean oil, sunflower oil, corn oil, and tung oil.

9. A modified vegetable triglyceride of claim 1, wherein said vegetable triglyceride is soybean oil.

10. A method for preparing a modified vegetable triglyceride characterized by the following formula:

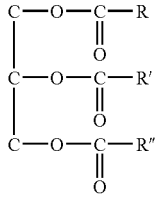

wherein R, R' and R" are independently selected from C-7 to C-21 aliphatic fatty acid residues, each including the structures:

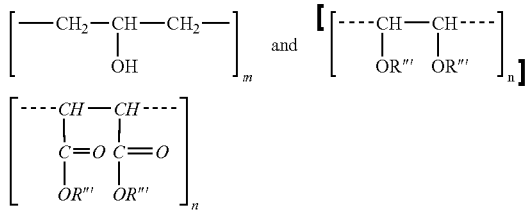

wherein R'" is H or C-2 to C-10 straight chain or branched hydrocarbon;

wherein the ratio of R'"=hydrocarbon:R'"=H in said modified triglyceride is at least 90:10;

wherein m=0–1;

wherein n=0–3; and wherein the average Σn for R, R' and R" in said modified triglyceride is at least 1;

the method comprising reacting an epoxidized vegetable triglyceride having at least one oxirane ring structure with an anhydride selected from the group consisting of acetic, propionic, butyric, valeric, hexanoic, heptanoic, octanoic, nonanoic and n-decanoic in the presence of a suitable catalyst for simultaneously opening the oxirane ring and activating the anhydride in order to convert each of said oxirane ring structures to a diester derivative.

11. The method of claim 10, wherein said catalyst is boron trifluride etherate.

12. The method of claim 11, wherein said reacting takes place a temperature of at least 40° C.

13. The method of claim 10, wherein said epoxidized vegetable triglyceride is epoxidized soybean oil.

14. The method of claim 10, wherein said anhydride is hexanoic anhydride.

15. A method for preparing a modified vegetable triglyceride characterized by the following formula:

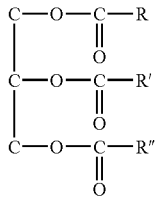

wherein R, R' and R" are independently selected from C-7 to C-21 aliphatic fatty acid residues, each including the structures:

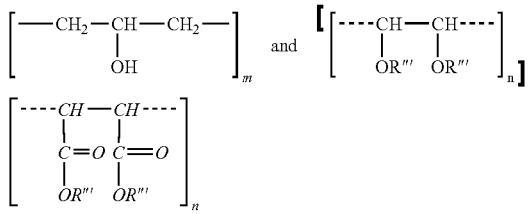

wherein R'" is H or C-2 to C-10 straight chain or branched hydrocarbon;

wherein the ratio of R'"=hydrocarbon:R'"=H in said modified triglyceride is at least 90:10;

wherein m=0"1;

wherein n=0"3; and wherein the average Σn for R, R' and R" in said modified triglyceride is at least 1;

the method comprising:

a. refluxing an epoxidized vegetable triglyceride having oxirane ring structures in an aqueous solvent in the presence of a strong acid catalyst in order to hydrolyze the oxirane ring to a dihydroxy intermediate;

b. reacting said dihydroxy intermediate with an anhydride selected from the group consisting of acetic, propionic, butyric, valeric, hexanoic, heptanoic, octanoic, nonanoic and n-decanoic in order to covert said dihydroxy intermediate to a diester derivative.

16. The method of claim 15, wherein said catalyst is perchloric acid.

17. The method of claim 15, wherein said refluxing in step (a) is conducted at approximately 100° C.

18. The method of claim 15, wherein said reacting in step (b) is conducted at room temperature.

19. The method of claim 15, wherein said epoxidized vegetable triglyceride is epoxidized soybean oil.

20. The method of claim 15 wherein said anhydride is hexanoic anhydride.

21. An industrial fluid comprising the modified vegetable triglyceride of claim 1 and another functional component.

22. The industrial fluid of claim 21, wherein said functional component is selected from the group consisting of extreme-pressure additive, anti-wear additive, pour point depressant, base stock, and diluent.

* * * * *